United States Patent [19]
McKay

[11] Patent Number: 5,666,947
[45] Date of Patent: Sep. 16, 1997

[54] FORMATION AND DELIVERY OF AN ATOMIZED LIQUID

[75] Inventor: Michael Leonard McKay, Kardinya, Australia

[73] Assignee: Orbital Engine Company (Australia) Pty. Limited, Balcatta, Australia

[21] Appl. No.: 615,287

[22] PCT Filed: Oct. 27, 1994

[86] PCT No.: PCT/AU94/00657

§ 371 Date: Mar. 27, 1996

§ 102(e) Date: Mar. 27, 1996

[87] PCT Pub. No.: WO95/11714

PCT Pub. Date: May 4, 1995

[30] Foreign Application Priority Data

Oct. 28, 1993 [AU] Australia ................ PM2079

[51] Int. Cl.[6] .................................................. B65D 83/14
[52] U.S. Cl. .......................... 128/200.21; 128/200.14; 128/205.13; 128/205.24; 128/205.18
[58] Field of Search .............. 128/200.14, 203.12, 128/203.13, 203.14, 204.18, 205.25, 200.21, 200.22, 200.28, 200.15, 203.23, 203.24, 203.28, 203.29, 205.13, 205.14, 205.24; 222/95, 105, 32.9, 319, 162

[56] References Cited

U.S. PATENT DOCUMENTS 3,979,027 9/1976 Loeffler ...................... 222/193
5,062,419 11/1991 Rider ........................ 128/200.21

FOREIGN PATENT DOCUMENTS 1703474  2/1972  Germany .
1279797  6/1972  United Kingdom .
1348200  3/1974  United Kingdom .
2084263  4/1982  United Kingdom .
2224447  5/1990  United Kingdom .

Primary Examiner—Vincent Millin
Assistant Examiner—Robert N. Wieland
Attorney, Agent, or Firm—Nikaido, Marmelstein, Murray & Oram LLP

[57] ABSTRACT

A method of delivering an atomised liquid including supplying a liquid to an admixing chamber (3,34), separately supplying a compressed gas to the admixing chamber (3,34), the compressed gas at least substantially completely evacuates the liquid held in the admixing chamber and delivering the liquid through an atomising device (4,5,60) to atomise the liquid, wherein the quantity of the liquid and the compressed gas supplied to the admixing chamber (3,34) is controlled to thereby maintain a predetermined mass ratio of the liquid and the supplied compressed gas. An apparatus for delivering an atomised liquid including a liquid supply device (6,24) for supplying liquid to an admixing chamber (3,34), a gas supply device (2,33) for separately supplying compressed gas to the admixing chamber (3,34), and an atomising device (4,5,60) for atomising the liquid evacuated by the supplied compressed gas, wherein the liquid supply device (6,24) supplies a predetermined quantity of liquid at each actuation of the apparatus and the gas supply device (2,33) controls the quantity of gas supplied to the admixing chamber (3,34) to thereby maintain a predetermined mass ratio of the liquid and the supplied compressed gas.

41 Claims, 8 Drawing Sheets

FORMATION AND DELIVERY OF AN ATOMIZED LIQUID

This invention relates to a method and apparatus for the formation and delivery of an atomised liquid. This invention is applicable for administering a drug dosage to a human or an animal by way of inhalation of the drug dosage through the respiratory tract.

It is well known to administer drugs to humans through the respiratory tract. Conventional methods of such administration utilise inhalers which the user places in the mouth and inhales during the release of the drug dosage from the inhaler. Such inhalers normally use Freon as the means by which the drug is sprayed into the mouth of the user. The drug to be administered is either dissolved or carried in solid or liquid suspension by the Freon. Upon release from the inhaler, the Freon vaporises and propels the drug into the users mouth.

Normally, the effectiveness of the drug is related to the amount of the drug that actually passes through the mouth and throat of the user and which is deposited on the lower respiratory tract. It is common to define the effectiveness of the drug delivery system in terms of "percentage respirable dose". The higher the percentage respirable dose, the better the ability of the system to deliver the drug to where it is most effective. Apart from the obvious benefits of having a high percentage respirable dose in that there is less wastage of what in many instances is a relatively expensive respirable drug, there is an additional benefit in that there will be reduced side-effects from the respirable drug being absorbed in the mouth or upper respiratory tract or being transported to the users digestive system. Futher, there is at the present time an imperative for new systems of administering a drug dosage to humans or animals which preferably do not use propellants such as Freon (which is believed to be environmentally harmful due to its effects on the earth's ozone layer) and which are capable of achieving the required percentage respirable dose. It is therefore an object of the present invention to provide an improved method and apparatus for delivering atomised liquids. A preferred object is to provide a method and apparatus for delivering a respirable drug capable of achieving a high percentage respirable dose.

The present invention therefore provides in one aspect a method of delivering an atomised liquid including supplying a liquid to an admixing chamber, separately supplying a compressed gas to the admixing chamber, the compressed gas at least substantially completely evacuating the liquid held in the admixing chamber and delivering the liquid through an atomising means to atomise the liquid, wherein the quantity of the liquid and the compressed gas supplied to the admixing chamber is controlled to thereby maintain a predetermined mass ratio of the liquid and the supplied compressed gas.

Liquid may be supplied to the admixing chamber subsequent to the compressed gas. Alternatively, compressed gas may be supplied to the admixing chamber subsequent to the liquid. The compressed gas may completely entrain the liquid held within the admixing chamber. The gas may conveniently be air although other gases are also envisaged. Preferably, the liquid contains a drug in solution or in liquid or solid suspension for administering to the respiratory tract of a human or an animal. Preferably, the contents of the admixing chamber pass through the atomising means for a predetermined duration which is less than the normal duration of the inhalation event of a human or an animal.

Preferably, the predetermined amount and pressure of the compressed gas is selected so that the entire contents of the admixing chamber are passed through the atomising means in a time period which is less than the duration of the normal inhalation event of the human or animal. In one form of the invention, it is possible for this time period to be adjusted to suit the individual user.

Preferably, the particle size distribution of the atomised liquid produced by release of the contents of the admixing chamber through the atomising means is such that sufficiently small particles are created so as to be readily transported to the desired part of the human's or animal's respiratory tract during the inhalation event. In the case of humans, particle sizes of less than 10 microns are desirable and particles sizes of less than 6 microns are even more desirable.

According to another aspect of the present invention, there is provided an apparatus for delivering an atomised liquid including a liquid supply means for supplying liquid to an admixing chamber, a gas supply means for separately supplying compressed gas to the admixing chamber, and an atomising means for atomising the liquid evacuated by the supplied compressed gas, wherein the liquid supply means supplies a predetermined quantity of liquid at each actuation of the apparatus and the gas supply means controls the quantity of gas supplied to the admixing chamber to thereby maintain a predetermined mass ratio of the liquid and the supplied compressed gas.

The compressed gas may completely entrain the liquid held within the admixing chamber. Preferably, the gas supply means for supplying a predetermined amount of compressed gas to the admixing chamber includes a gas reservoir for containing a gas at a predetermined first pressure and a valve means separating said gas reservoir from said atomising means, said valve means being operable so as to allow the gas to flow from the gas reservoir through the admixing chamber and the atomising means until a second pressure level is achieved due to the substantial equilibrium being achieved between the atmospheric pressure and the pressure in the gas reservoir. The gas reservoir may have a set volume which contains an at least substantially predetermined mass of gas when the compressed gas is at the predetermined first pressure. The compressed gas may be provided by a compressor pump communicating with the gas reservoir. The compressed gas may be supplied through a non-return valve into the gas reservoir. The rate of supply of compressed gas to the admixing chamber may be significantly greater than the rate of supply of compressed gas from the compressor pump to the gas reservoir.

In an alternative embodiment, the gas supply means may include a gas reservoir for the supply of gas at a predetermined first pressure, valve means being provided between the gas reservoir and the atomising means and being operable to control the admixture and evacuation of the liquid and the gas in the admixing chamber, the required control over the mass of gas being achieved at each actuation of the apparatus by controlling the duration of the opening of the valve means to admit gas to the atomising means so as to control the quantity of gas delivered in relation to the fixed mass of liquid dispensed into the admixing chamber, a predetermined second pressure being defined at the closure of the said valve means at the end of the actuation of the apparatus. The predetermined second pressure may be a function of the size of the gas reservoir relative to the size of the restriction of the atomising means.

The atomising means may preferably be an atomising nozzle having a circular throat portion with a preferred throat diameter lying in the range of between 0.15 millimetres to 0.35 millimetres. A downstream divergent duct may be provided expanding out from the throat portion at an included angle lying between 2 degrees and 8 degrees. The axial length of the divergent portion downstream of the throat diameter may preferably be between 0.5 millimetres and 5 millimetres.

Actuation means may be provided for displacement of the valve means. The actuation means may include a pushrod for displacing the valve means. The pushrod may be moved by way of a solenoid actuator. Alternatively, the actuation means may include a manually actuated pushrod.

The liquid supply means preferably includes a flexible bladder for containing the liquid, a body member having a liquid chamber in communication with the flexible bladder, a piston means supported within the liquid chamber for pumping liquid contained within the liquid chamber to the admixing chamber, and a protective outer shroud for enclosing the flexible bladder and body member, wherein displacement of the outer shroud produces a relative displacement of the piston within the liquid chamber to thereby pump the liquid from the liquid chamber. A continuing displacement of the outer shroud preferably subsequently results in displacement of the pushrod after the liquid has been pumped from the liquid chamber into the admixing chamber. The pushrod may include an elongate passage therethrough and at least one discharge orifice extending therefrom, the liquid being pumped through the elongate passage and out of the discharge orifice into the admixing chamber. A floating valve ring may preferably be provided in a annular groove in said piston, the floating valve ring sealing the fluid chamber when the piston is displaced in a first direction, and allowing fluid communication with the fluid chamber when the piston is displaced in an opposing direction thereof.

According to another aspect of the invention, there is provided a liquid metering device including a flexible bladder for containing liquid, the flexible bladder surrounding a body member having a liquid chamber therein, the liquid chamber being in fluid communication with the interior of the flexible bladder, an outer shroud for containing the flexible bladder and the body member, a piston supported within the liquid chamber for pumping liquid therefrom, and a pushrod extending from the piston, wherein movement of the outer shroud relative to the piston results in relative displacement of the piston within the liquid chamber to thereby pump liquid from the liquid chamber. The pushrod may be displaced together with the piston after the liquid has been pumped from the liquid chamber.

The piston may be integral with the pushrod. Alternatively, in another embodiment, the piston may be integral with the body member, the liquid chamber being provided within the pushrod. The pushrod may include an elongate passage passing therethrough, the pumped liquid passing through the passage to at least one discharge orifice provided on the pushrod. A non-return valve may be supported within the passage for controlling the direction of flow of liquid therethrough.

The apparatus may include a floating valve ring provided in an annular groove in the piston, the floating valve ring sealing the liquid camber when the piston is displaced in a first direction, and allwing fluid communiation with the liquid chamber when the piston is displaced in an opposing direction thereof.

It has been found that the method and apparatus of the present invention may atomise liquids such as water or alcohol such that the particles produced in the resultant spray may not impinge in the upper regions of the throat of the user to the same extent as found in existing metered dose inhaler apparatus using liquid Freon propellents to disperse drug agents in a spray developed by rapid evaporation of a liquid propellent.

It has also been found that in relation to the method and apparatus of the present invention, a constant gas pressure is not as important to the function of the apparatus as the requirement of a controlled ratio of the mass of gas relative to the mass of dispersed liquid to pass through the atomising nozzle, even though gas pressure may be a convenient means of specifying a gas mass in the apparatus which may be dispensed during an inhalation event. The temperature of the gas is of secondary importance and, in practice, the temperature of the portable apparatus is typically in the relatively narrow range of environmental conditions defined by the comfort conditions of typical human patients.

It will be of convenience to further describe the invention by reference to the accompanying drawings which illustrate possible embodiments of the invention. Other embodiments of the invention are possible and consequently the particularity of the accompanying drawings is not to be understood as superseding the generality of the preceding description of the invention.

Figure 1:
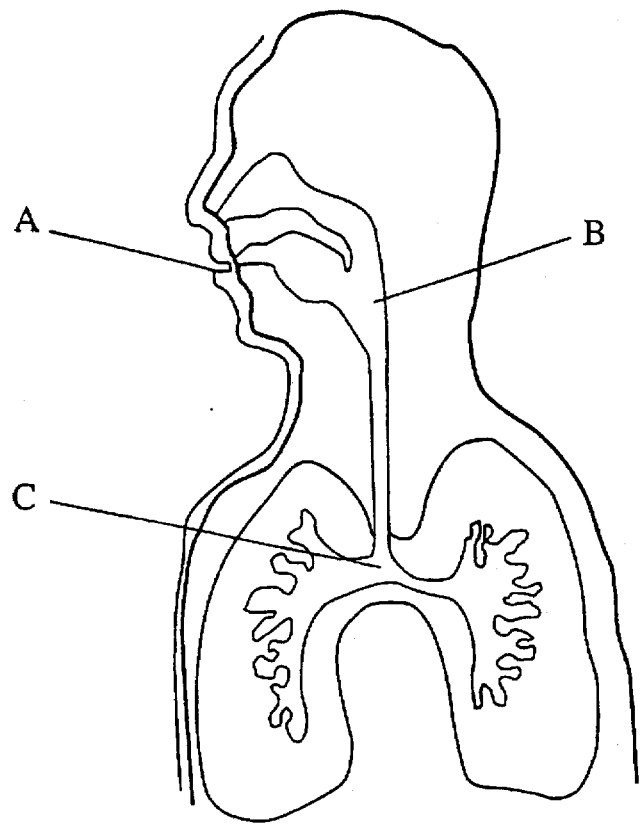
FIG. 1 shows a diagrammatic representation of the human respiratory tract.

Referring initially to FIG. 1, label A refers to the mouth of a human patient into which the spray nozzle is inserted at each dosing event. Label B refers to the throat region where a large portion of a spray may impinge and not reach the lower regions of the respiratory tract. Label C refers to the general region where the drug is to be deposited. The respirable dose passes to this general region, while the impinged portion in the throat may pass to the digestive system and cause certain unwanted side effects in a patient.

Figure 2:
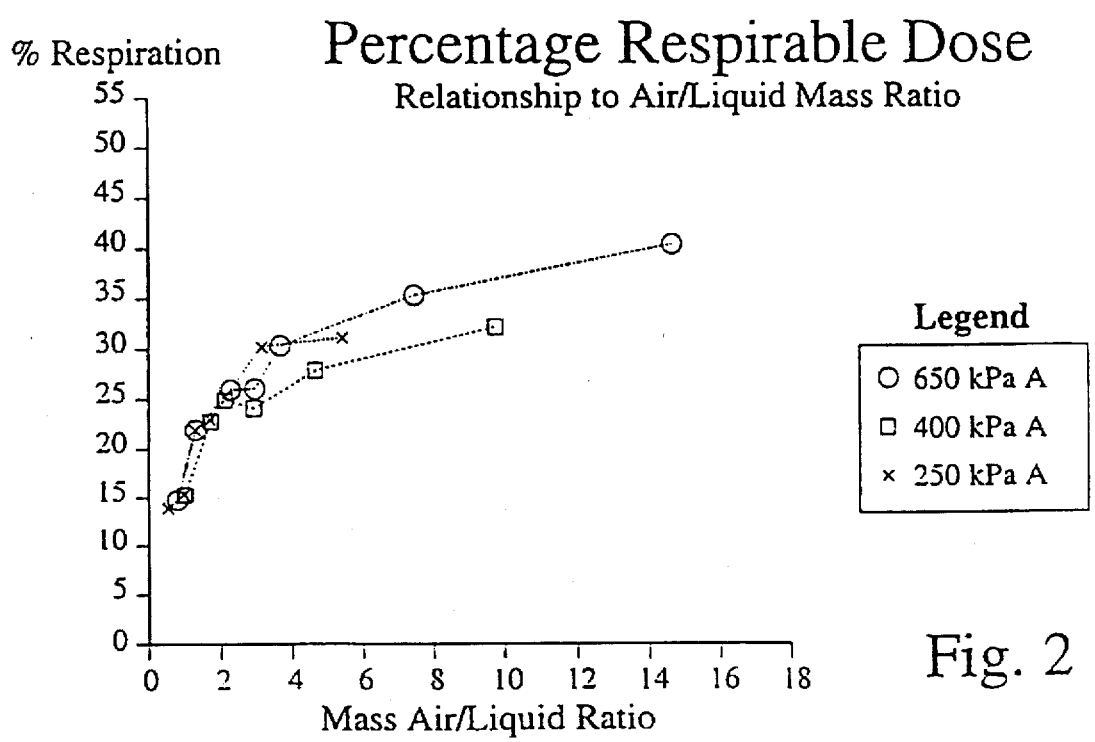
FIG. 2 shows a graph showing the Percentage Respirable Dose against the ratio of Mass of Air to Mass of Liquid.

Regarding FIG. 2, there is shown a graph detailing the experimental information derived from analytical tests of an embodiment of this invention to atomise aqueous sprays. In FIG. 2 it may be derived that the control over the mass ratio results in effective control over the percentage of the spray which is respirable by the patient. Further, the droplet size distribution produced by the nozzle means described in this invention results in a high maximum percentage respirable dose due to the small droplets produced. It is noted that higher mass air/liquid ratios provide significant improvements in the respirable dose possible.

Figure 3:
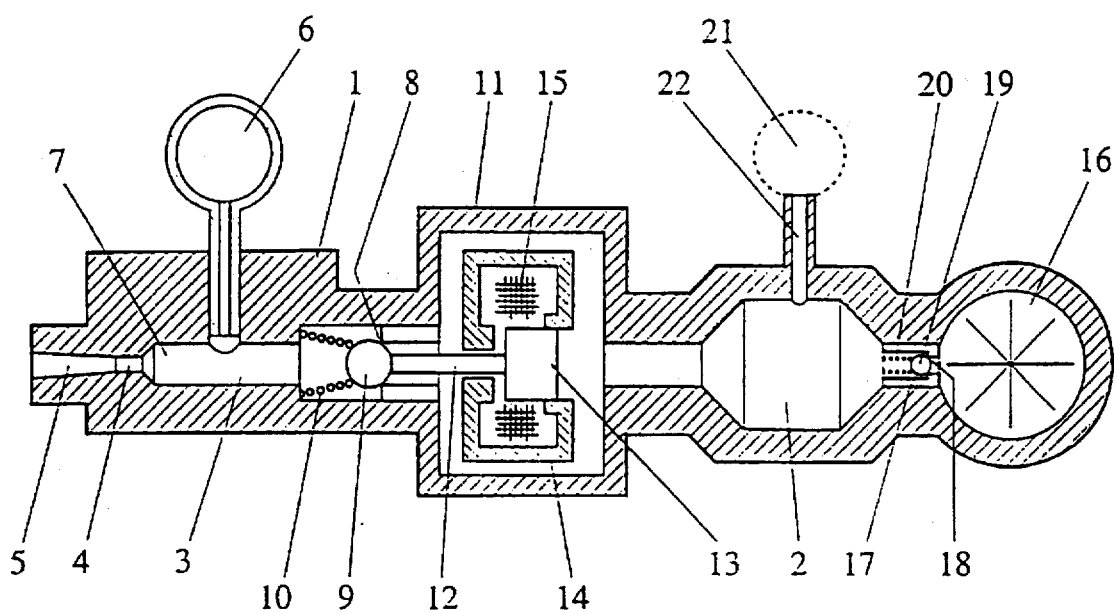
FIG. 3 shows a diagrammatic representation of a first embodiment of the apparatus according to the present invention.

Referring to FIG. 3, a first embodiment of the apparatus is illustrated showing an atomiser body 1 having a reservoir 2 which supplies gas to an admixing chamber 3, into which a discrete dose of liquid may be dispensed from the liquid metering device entrain from the reservoir 2 may entrain the liquid in the space 7 leading to the throat 4 of the atomising nozzle. The divergent duct 5 downstream of the throat 4 provides the final path of the atomised liquid and gas which are ultimately directed entirely to the mouth A of the human patient depicted in FIG. 1. Valve means are provided in the path between the reservoir 2 and the throat 4 of the atomising nozzle, such means being defined by the spherical valve element 9 which is normally urged into sealing engagement with the valve seat 8 by the spring 10.

A solenoid 11 having a ferromagnetic path 14, windings 15 and a movable armature 13 with an integral pushrod 12 is used to control the gas flow to the admixing chamber 3. The solenoid 11 is actuated by applying an electric current to the windings 15 so as to provide an electromotive force on the armature 13. This force is transmitted by the pushrod 12 to overcome the force of the spring 10 acting on the valve element 9 and to thereby allow gas to flow from the reservoir 2 to the admixing chamber 3.

The quantity of gas supplied during an actuation event of the solenoid 11 is controlled by the volume of the reservoir 2 and the pressure to which the reservoir 2 is charged by the compressor pump 16. A non-return valve 17 is provided between the compressor pump 16 and the reservoir 2 and includes a spherical valve element 19 acting on a sealing seat 18 due to the force imparted thereto by the spring 20.

The pressure supplied to the reservoir 2 may be controlled by regulating the actuation of the compressor pump 16 by sensing the pressure in the reservoir 2 with the sensor 21 connected by a duct 22 to the reservoir 2. In practice, the pressure sensor 21 may take the form of a pressure-sensitive switch controlling the flow of electrical current to the compressor pump 16 so that the compressor pump 16 is deactivated when a sufficiently high pressure is reached.

The rate of re-supply of gas to the reservoir 2 is conveniently lower than the rate at which the gas is drained during an actuation event of the solenoid 11, so that the pressure in the reservoir 2 falls to a low value close to the equilibrium pressure with atmospheric pressure downstream of the nozzle duct 5. The mass of gas supplied to the admixing chamber 3 is thus relatively dependent on the size of the reservoir 2 and the pressure to which it is charged at the start of the actuation event. The mass of gas supplied is relatively independent of the smaller rate of supply which is available from the compressor pump 16.

Alternatively, the reservoir 2 may be made of sufficient size to drop in pressure by a predetermined amount in response to an actuation event of the solenoid 11, where the duration of the current flowing in the windings 15 may be controlled so as to limit the mass of gas delivered to the admixing chamber 3.

In relation to the atomising nozzle, the nozzle has a diverging section 5 downstream of the restrictive throat 4, which has a desirable effect in obtaining the atomisation demonstrated in this apparatus, the efficiency of which is partly due to the high velocity of the gas flow which is produced by the divergent section. Also, the diverging portion is desirable in simplifying the manufacture of the nozzle by low-cost techniques.

Figure 4:
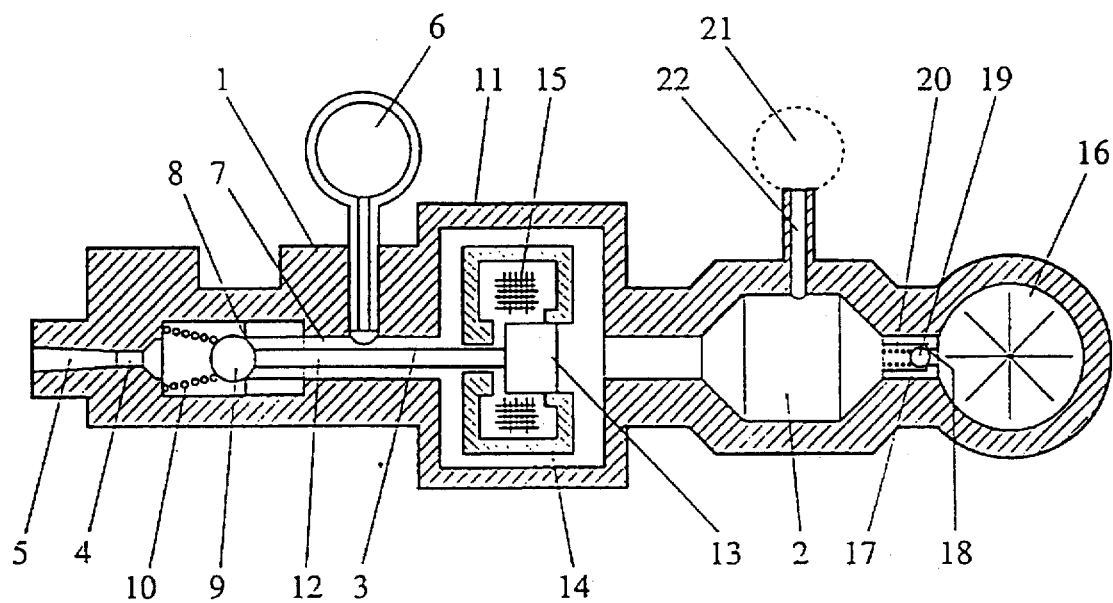
FIG. 4 shows a diagrammatic representation of a second embodiment of the apparatus according to the present invention.

As shown in FIG. 4, the valve element 9 and associated seat 8 and spring 10 may be alternatively located downstream of the location of the introduction of the liquid from the liquid metering device 6. All other details and principles of operation are similar to the corresponding parts as enumerated in FIG. 3.

Figure 5:
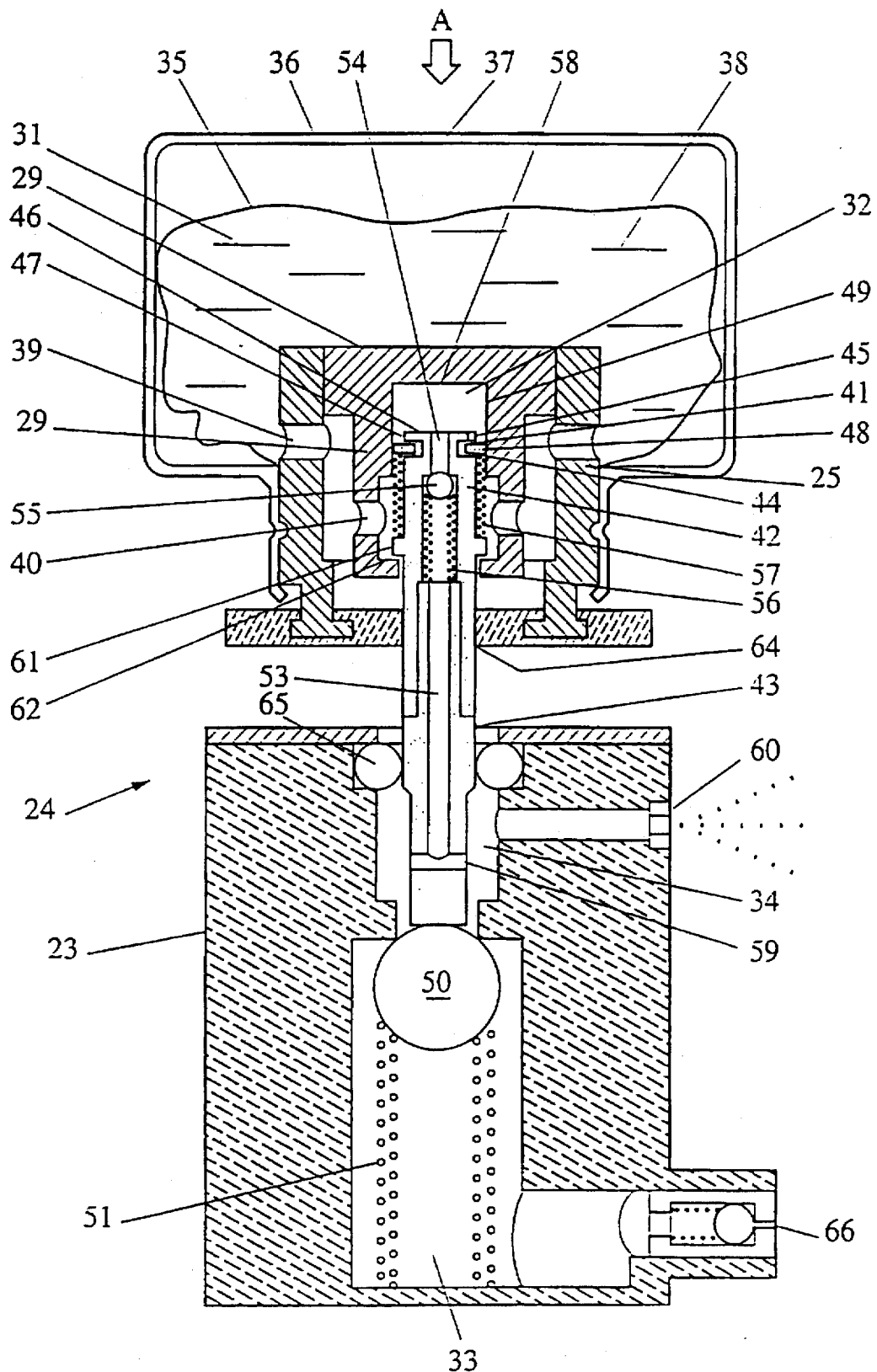
FIG. 5 shows a diagrammatic representation of a third embodiment of the apparatus according to the present invention.
Figure 6:
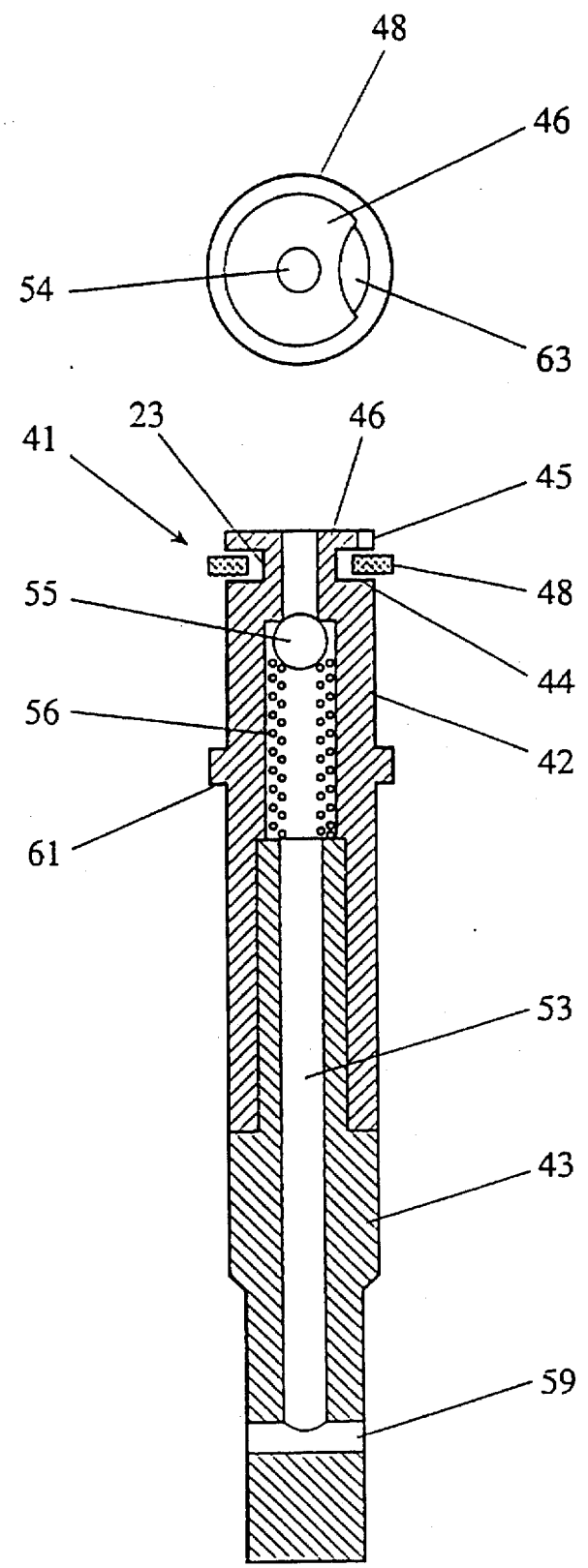
FIG. 6 shows the pushrod and piston assembly of the apparatus of FIG. 5.

The above two embodiments of the invention are particularly applicable for automatic operation because a solenoid valve 14 is used to actuate the valve element 9. It is however also possible to have a manually actuated apparatus as shown in FIGS. 5 and 6. Referring initially to FIG. 5, the liquid metering device 24 of the apparatus includes a first chamber 31 for storing liquid 38, and a second chamber 32 provided within a cylindrical body 29 in fluid communication with the first chamber 31. A gas reservoir 33 and an admixing chamber 34 are provided in a base portion 23 of the apparatus.

The first chamber 31 is formed by a flexible plastic bladder 35 contained within a protective outer shroud 36 with at least one vent hole 37 which allows atmospheric pressure to bear upon the first chamber 31. The liquid 38 to be dispensed is contained within the first chamber 31 and communicates with the second chamber 32 through holes 39 and 40 provided through a collar 25 surrounding the cylindrical body 29 and the piston valve port 41. The second chamber 32 provides metering of the mass of liquid supplied to the admixing chamber 34.

As shown in FIG. 6, the piston valve port 41 includes a piston 42, which is effectively an extension of the pushrod 43. The piston 42 has an annular groove 23 at the upper end thereof which defines two separate pressure lands, the sealing land 44 and the retraction land 45. The retraction land 45 is part of a crown 46 which allows fluid to always pass through the clearance 47 between the crown 46 and the bore 49 of the pumping chamber defining the second chamber 32. A flexible valve ring 48 is engaged in the bore 49 and selectively cooperates between the aforementioned pressure lands 44 and 45, the actual contact of the valve ring 48 with the respective lands 44 and 45 depending on the direction of relative motion of the piston 42 within the bore 49. Because the valve ring 48 does not fill the groove 23, only one of the respective lands 44 or 45 can be in axial contact with the sealing ring 48 at any one time.

During a pumping stroke, the entire shroud 36 and associated parts, including the bore 49 are moved by manual axial force in the general direction indicated by the arrow A. A reaction force maintained on the pushrod 43 by the valve member 50 and associated spring 51 of FIG. 5 results in the volume of the second chamber 32 decreasing and the valve ring 48 making contact with the sealing land 44. Because the volume decreases in the second chamber 32, the liquid pressure rises to such an extent that the relief valve 55 becomes unseated, allowing liquid to pass from the second chamber 32, past the port 54 and the relief valve 55, through the coils of the spring 56 and into the pushrod duct 53. The spring 57 is compressed as the delivery stroke continues, until the piston crown 46 makes contact with the stop face 58. Up to this event, the liquid dose passes from the pushrod duct 53, through the orifices 59 and into the admixing chamber 34, which is normally in equilibrium with atmospheric pressure due to the discharge port 60 communicating with the atmosphere.

At this point the axial force exerted by the pushrod 43 may overcome the combined forces on the valve element 50 due to the spring 51 and the elevated gas pressure in the gas reservoir 33. The valve element 50 may open and allow high pressure gas in the gas reservoir 33 to escape into the admixing chamber 34 and entrain the liquid 38 therein as the gas moves to the venting discharge port 60 as the pressure equilibrium is achieved. Atomisation is achieved across the discharge port 60 as the relatively higher velocity gas moves over the surface of the relatively lower velocity liquid.

The stored quantity of gas in the gas reservoir 33 is of a discrete quantity due to the fixed volume of the reservoir 33 and a relatively fixed pressure and temperature, although very close control over pressure and temperature is not strictly required for the purposes of this invention. The pressure may be achieved by an electrically-driven compressor or hand pump.

When the manual actuation of the shroud 36 is released, the return spring 57 returns the piston 42 to the quiescent position defined by contact of the land 61 on the piston 42 with the land 62 on the bore 49. In fact, the shroud 36 and associated parts move vertically in the sense of FIG. 5. As the piston 42 and shroud 36 move in the direction urged by the spring 57, the valve ring 48 makes contact on the retraction land 45. Liquid is allowed to enter the second chamber 32 past the defined port 63 in the piston crown 46. In this state, the quiescent state, liquid may fill the second chamber 32 in preparation for the next delivery stroke.

Seal 64 and seal 65 act to prevent the escape of fluids in an obvious manner.

It is envisaged that more than one port 63 may be used in the crown 46 and that various shapes may be used to the same effect as the one detail shown in FIG. 6.

Furthermore, it is envisaged that an improved discharge port 60 may be employed to obtain optimum atomisation. The surface area exposed to the liquid may be increased relative to the exit area of the port 60, thereby increasing the velocity of the gas and liquid relative to one another, thus improving the atomisation. Alternatively, an atomisation nozzle as shown in FIGS. 3 and 4 could be used.

The gas supply to the reservoir 33 may be accomplished by a positive-displacement air pump driven by an electric motor or solenoid which may fill the chamber relatively slowly between actuation events, the control of which may be exercised by turning off the electric pump when the pressure in the chamber has reached a predetermined pressure. The air supply to the reservoir 33 through the check valve 66 may be retained between air pumping events by the non-return characteristics of the check valve 66.

The above described arrangement allows actuation of the apparatus even when the apparatus is held in a position away from vertical. The liquid metering device 24 meters the correct amount of liquid and is unaffected by the orientation of the apparatus. Furthermore, the storing of the liquid 38 within the flexible bladder 35 helps to ensure that the liquid 38 remains sterile. Once the flexible bladder 35 is fully emptied of liquid 38, the liquid metering device 24 can optionally be disposed of and replaced with a new liquid metering device.

Figure 7:
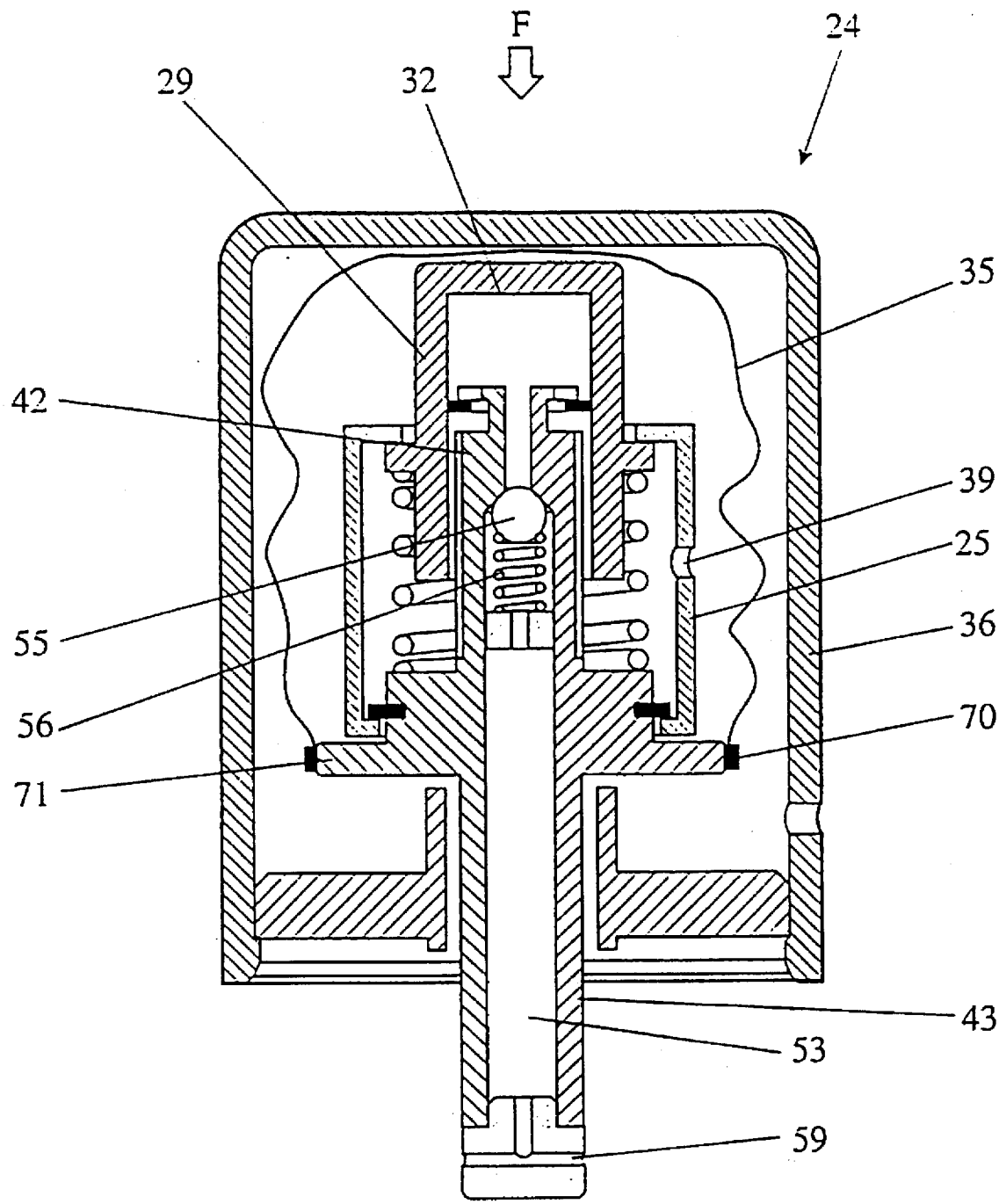
FIGS. 7 to 10 show alternative embodiments of the liquid metering device according to the present invention.
Figure 8:
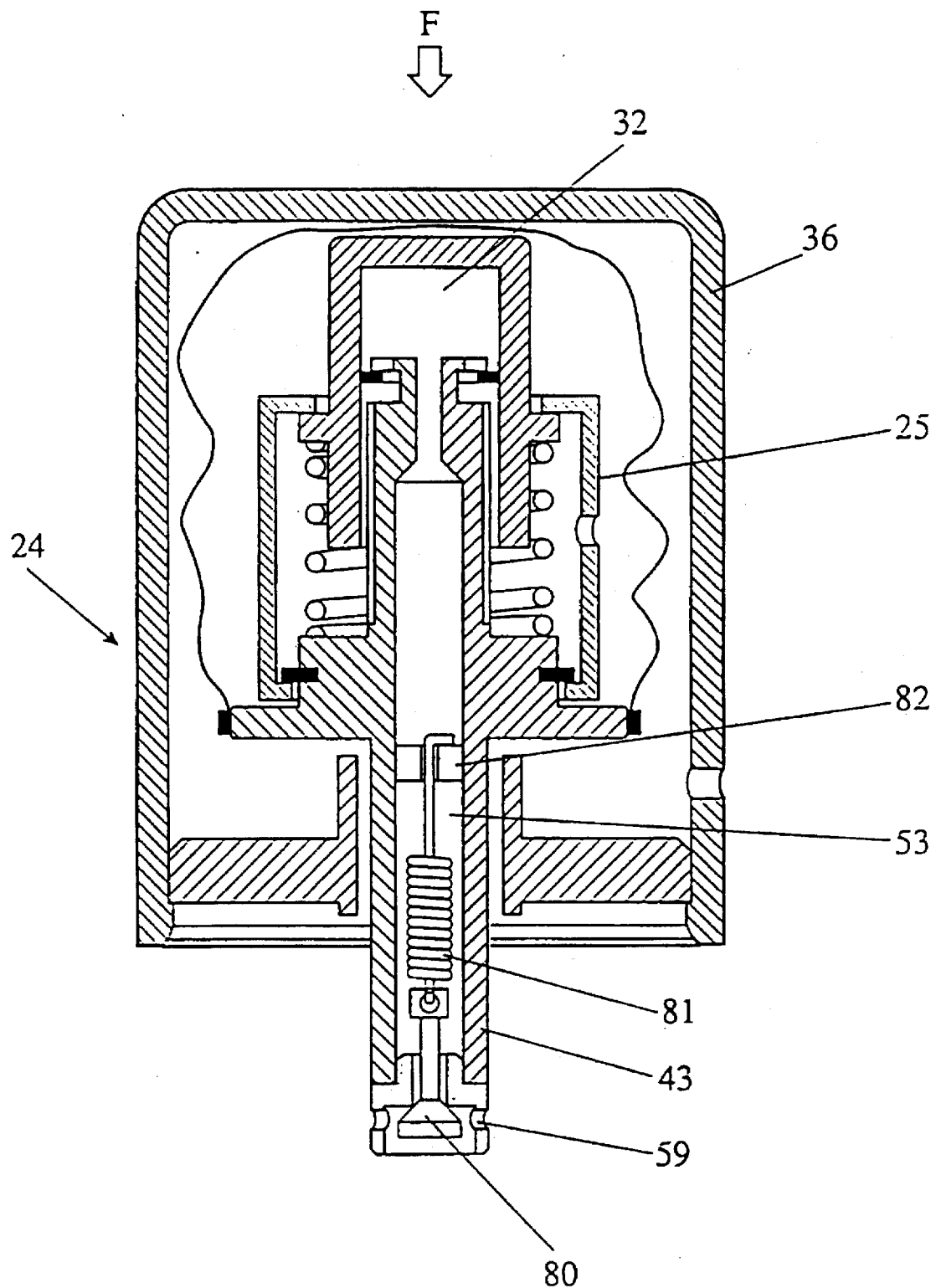

Alternative embodiments of the liquid metering device 24 are shown in FIGS. 7 to 10, with like reference numerals being used for corresponding features. In the embodiment shown in FIG. 7, the primary difference is that the flexible bladder 35 is affixed by a ring 70 to a radially extending member 71 of the pushrod 43. This provides a more secure seal for the flexible bladder 35 as well as making the liquid metering device 24 more easy to manufacture. The liquid in the pushrod duct 53 maybe retained therein between actuation events by the surface tension of the liquid within the discharge orifices 59. Alternatively, the liquid metering device 24 may be designed to positively contain the liquid within the pushrod duct 53 close to the discharge orifices 59. Such a construction is shown in FIG. 8.

In FIG. 8, the check valve element 80 is in the form of a poppet valve located close to and normally closing the discharge orifices 59. A tension spring 81 is supported between a spring mount 82 located within the pushrod duct 53 and the check valve element 80. This arrangement maintains the fluid within the pushrod duct 53 until the liquid is to be dispensed. It is envisaged that the collar 25 may be constructed of a ductile and malleable material which may be deformed during assembly in order to calibrate the stroke of the pump to a defined and accurately-specified value. Furthermore, the accurately-specified stroke may be varied for different applications requiring different amounts of dispensed fluid.

The alternative embodiment in FIG. 8 is however not as accurate in terms of delivered liquid volume as the embodiment shown in FIG. 7 but is more easily adjusted by external apparatus after the final assembly of the liquid metering device 24.

Figure 9:
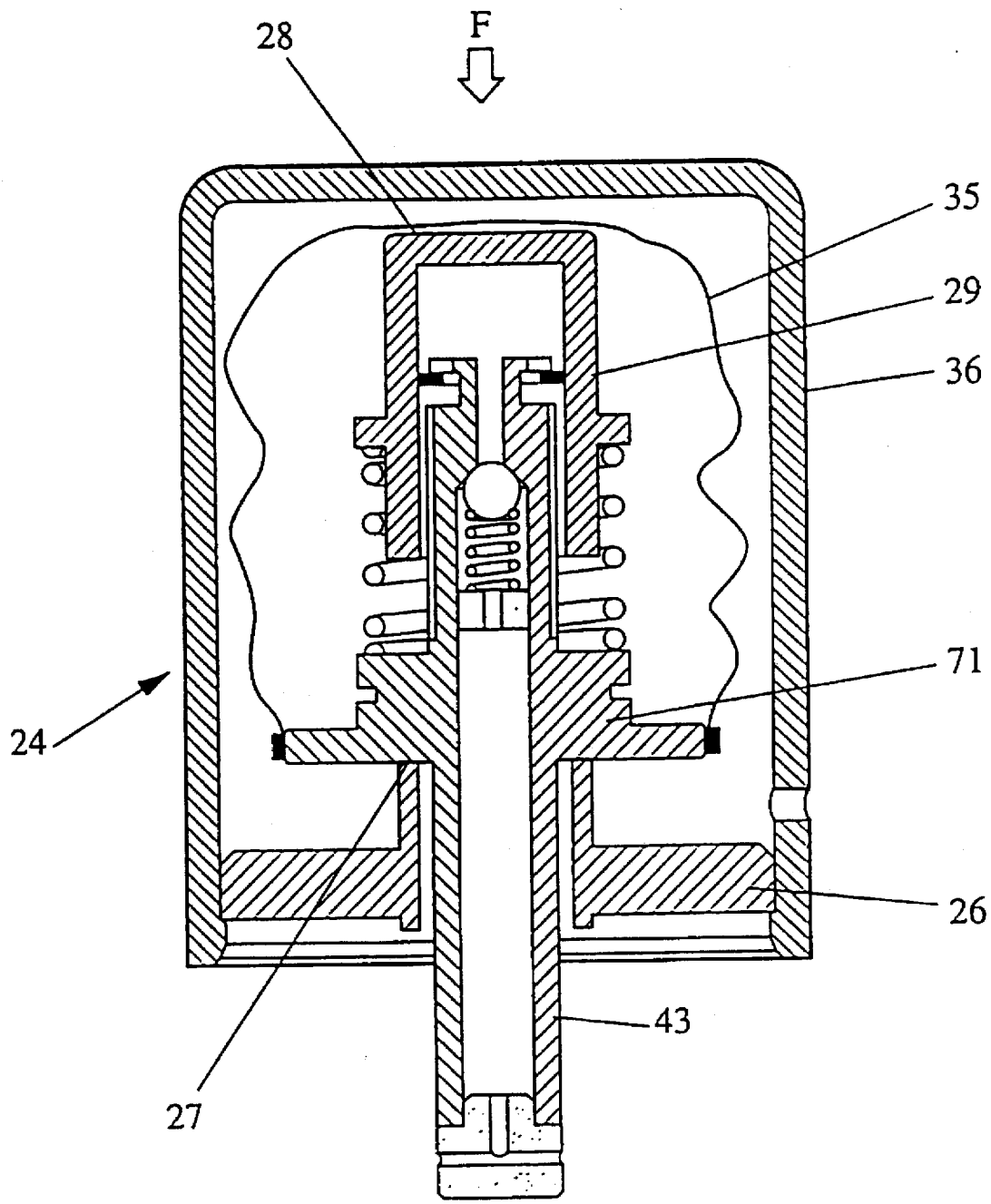

FIG. 9 shows another embodiment where the collar 25 of the previous embodiments is replaced in function by the external protective outer shroud 36 and an end piece 26 closing off the bottom end of the shroud 36. In this construction the stroke is limited by the contact of a land 27 provided on the end-piece 26 with the radial extending member 71 of the pushrod 43 and the alternative contact of the outer shroud 36 with a contact portion of the bladder 35, and the top 28 of the cylinder body 29. The axial position of the end-piece 26 within the shroud 36 may be varied to obtain various delivered quantities of fluid.

To improve the reliability of the sealing of the bladder 35, the portion of the bladder 35 contacting the outer shroud 36 may be formed from a rigid section of stronger material so that the contact force (F) is transmitted over a greater area and there is less chance of damage to the bladder 35.

Figure 10:
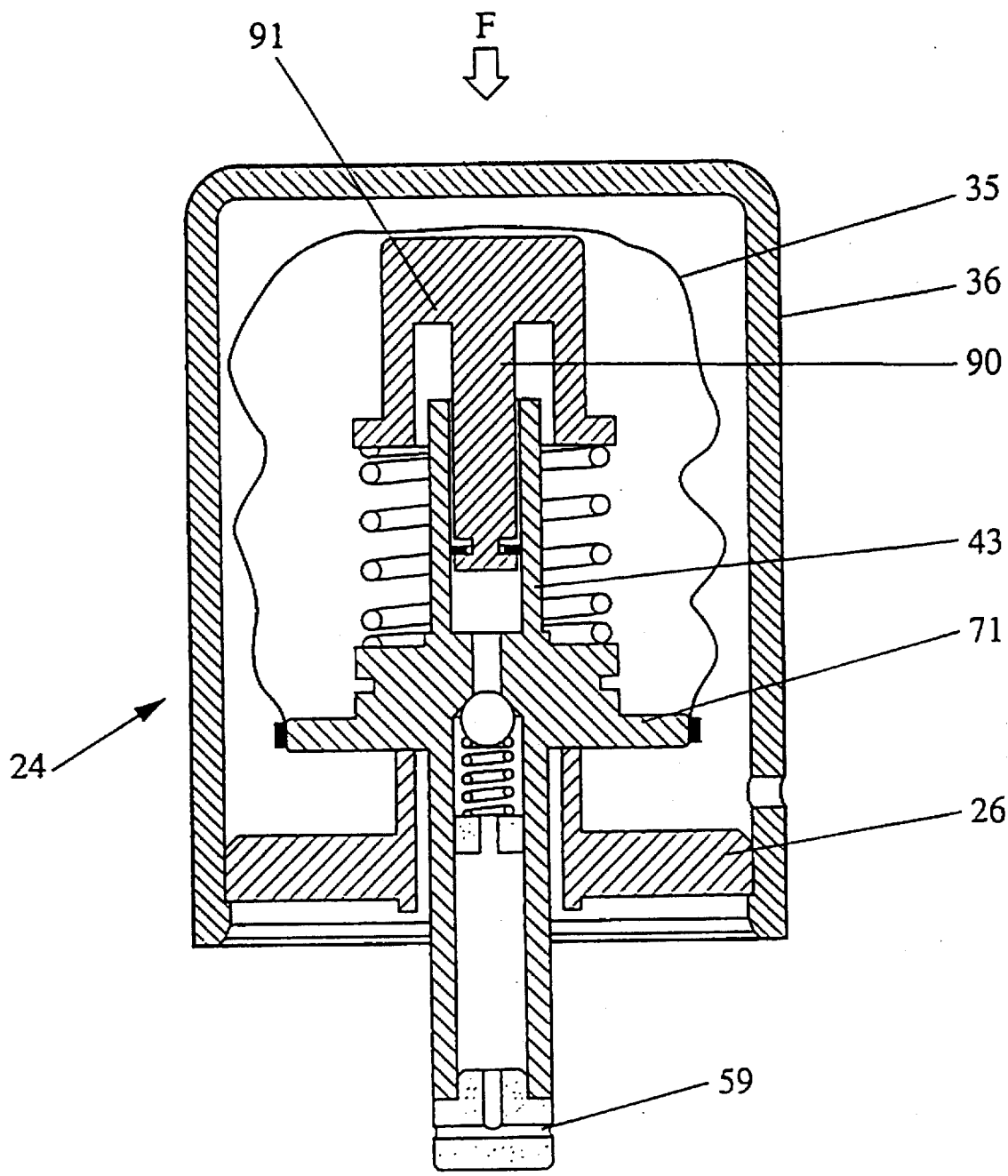

In the variant shown in FIG. 10, the piston 90 is a separate component from the pushrod 43 with the piston bore being provided within the pushrod 43. The liquid metering device 24 is otherwise functionally equivalent to the embodiment of FIG. 9.

Although the embodiments and description of the invention have concentrated on respiratory drug administration to human or animal patients, it will be appreciated that the invention contemplates other applications where there is a desire to administer accurate amounts of a liquid in a discrete form by using a compressed gas such as air.

The claims defining the invention are as follows:

1. A method of delivering an atomised liquid including supplying a liquid to an admixing chamber, separately supplying a compressed gas to the admixing chamber, the compressed gas at least substantially completely evacuating the liquid held in the admixing chamber and delivering the liquid through an atomising means to atomise the liquid, wherein the quantity of the liquid and the compressed gas supplied to the admixing chamber is controlled to thereby maintain a predetermined mass ratio of the liquid and the supplied compressed gas.

2. A method according to claim 1 liquid is supplied to the admixing chamber subsequent to the compressed gas.

3. A method according to claim 1 wherein compressed gas is supplied to the admixing chamber subsequent to the liquid.

4. A method according to claim 1 wherein the compressed gas entrains the liquid held in the admixing chamber.

5. A method according to claim 1 wherein the liquid is a respiratory drug for administering to the respiratory tract of a human or animal.

6. A method according to claim 1 wherein at least a portion of the contents of the admixing chamber pass through the atomising means for a predetermined duration less than the normal duration of the inhalation event of a human or animal.

7. A method according to claim 1 wherein the entire contents of the admixing chamber pass through the atomising means in a predetermined duration which is less than the duration of the normal inhalation event of a human or animal.

8. A method according to claim 6 wherein the predetermined duration is adjustable.

9. A method according to claim 1 wherein the average particle size of the atomised liquid is less than 10 microns, preferably less than 6 microns.

10. A method according to claim 1 wherein the compressed gas is air.

11. An apparatus for delivering an atomised liquid including a liquid supply means for supplying liquid to an admixing chamber, a gas supply means for separately supplying compressed gas to the admixing chamber, and an atomising means for atomising the liquid evacuated by the supplied compressed gas, wherein the liquid supply means supplies a predetermined quantity of liquid at each actuation of the apparatus and the gas supply means controls the quantity of gas supplied to the admixing chamber to thereby maintain a predetermined mass ratio of the liquid and the supplied compressed gas.

12. An apparatus according to claim 11 wherein the compressed gas entrains the liquid held in the admixing chamber.

13. An apparatus according to claim 11 wherein the gas supply means includes a gas reservoir for containing gas at a predetermined first pressure and a valve means separating said gas reservoir from said atomising means, said valve means being operable so as to allow the gas to flow from the gas reservoir through the admixing chamber and the atomising means until a second pressure level is reached within the gas reservoir.

14. An apparatus according to claim 13 wherein the second pressure level is at least substantially atmospheric pressure.

15. An apparatus according to claim 11 wherein the gas supply means includes a gas reservoir for containing gas at a predetermined first pressure, a valve means provided between the gas reservoir and the atomising means for controlling the admixture and evacuation of the liquid and the gas in the admixing chamber, the duration of opening of the valve means being controllable to thereby control the gas/liquid mass ratio.

16. An appartus as claimed in claim 15 wherein the compressed gas entrains the liquid held in the admixing chamber.

17. An apparatus according to claim 15, wherein the delivery of gas is ceased from the gas reservoir when the gas within the gas reservoir is at a predetermined second pressure, said predetermined second pressure being a function of the size of the gas reservoir relative to a size of a restriction of the atomising means.

18. An apparatus according to claim 13 including a compressor pump for supplying compressed gas to the gas reservoir, with a non-return valve provided between the compressor pump and the gas reservoir.

19. An apparatus according to claim 18 wherein the rate of supply of compressed gas from the gas reservoir to the admixing chamber is relatively higher than the rate of supply of compressed gas from the compressor pump to the gas reservoir.

20. An apparatus according to claim 13 wherein the atomising means is an atomising nozzle having a circular throat portion and a downstream divergent duct extending downstream therefrom.

21. An apparatus according to claim 20 wherein the throat portion has a diameter of between 0.15 to 0.35 millimetres.

22. An apparatus according to claim 20 wherein the divergent duct extends at an included angle of between 2 and 8 degrees.

23. An apparatus according to 20 wherein the axial length of the divergent duct is between 0.5 and 5.0 millimetres.

24. An apparatus according to claim 11 wherein the liquid supply means includes a flexible bladder for containing the liquid, a body member having a liquid chamber in communication with the flexible bladder, a piston supported within the liquid chamber for pumping liquid contained within the liquid chamber to the admixing chamber, and a protective outer shroud for enclosing the flexible bladder and body member, wherein displacement of the outer shroud produces a relative displacement of the piston means within the liquid chamber to thereby pump the liquid from the liquid chamber.

25. An apparatus according to claim 24 including a floating valve ring provided in an annular groove in said piston, the floating valve ring sealing the liquid chamber when the piston is displaced in a first direction, and allowing fluid communication with the liquid chamber when the piston is displaced in an opposing direction thereof.

26. An apparatus according to claim 25 including actuation means for displacement of the valve means.

27. An apparatus according to claim 26 wherein the actuation means includes a pushrod for displacing the valve means.

28. An apparatus according to claim 27, wherein a continuing displacement of the outer shroud subsequently results in displacement of the pushrod after the liquid has been pumped from the liquid chamber into the admixing chamber.

29. An apparatus according to claim 27 wherein the pushrod includes an elongate passage therethrough and at least one discharge orifice extending therefrom, the liquid being pumped through the elongate passage and out of the discharge orifice into the admixing chamber.

30. An apparatus according to any one of claims 27 wherein the pushrod is moved by means of a solenoid actuator.

31. An apparatus according to claim 26 wherein the actuation means includes a manually actuated pushrod.

32. A liquid metering device according to claim 27, wherein the pushrod is displaced together with the piston after the liquid has been pumped from the liquid chamber.

33. A liquid metering device according to claim 32, wherein the piston is integral with the pushrod.

34. A liquid metering device including a flexible bladder for containing liquid, the flexible bladder surrounding a body member having a liquid chamber therein, the liquid chamber being in fluid communication with the interior of the flexible bladder, an outer for containing the flexible bladder and the body member, a piston supported within the liquid chamber pumping liquid therefrom, and a pushrod extending from the piston, the piston being integral with the body member, the liquid chamber being provided within the pushrod. wherein movement of the outer shroud relative to the piston results in relative displacement of the piston within the liquid chamber to thereby pump liquid from the liquid chamber.

35. A liquid metering device according to claim 34, the pushrod including an elongate passage passing therethrough, the pumped liquid passing through the passage to at least one discharge orifice provided on the pushrod.

36. A liquid metering device according to claim 35 including a non-return valve supported within the passage for controlling the direction of flow of liquid therethrough.

37. A liquid metering device including a flexible bladder for containing liquid the flexible bladder surrounding a body member having a liquid chamber therein the liquid chamber being in fluid communication with the interior of the flexible bladder an outer for containing the flexible bladder and the body member, a piston supported within the liquid chamber for pumping liquid therefrom, a pushrod extending from the piston, and a floating valve ring provided in an annular groove in said piston, the floating valve ring sealing the liquid chamber when the piston is displaced in a first direction, and allowing fluid communication with the liquid chamber when the piston is displaced in an opposing direction thereof, wherein movement of the outer shroud relative to the piston results in relative displacement of the piston within the liquid chamber to thereby pump liquid from the liquid chamber.

38. A liquid metering device according to claim 37, wherein the piston is integral with the body member, the liquid chamber being provided within the pushrod.

39. A liquid metering device according to claim 37, the pushrod including an elongate passage passing therethrough, the pumped liquid passing through the passage to at least one discharge orifice provided on the pushrod.

40. A liquid metering device according to claim 39, including a non-return valve supported within the passage for controlling the direction of flow of liquid therethrough.

41. A liquid metering device according to claim 37, wherein the pushrod is displaced together with the piston after the liquid has been pumped from the liquid chamber.

* * * * *